United States Patent
Kang et al.

(10) Patent No.: US 10,602,956 B2
(45) Date of Patent: Mar. 31, 2020

(54) RADIATION DOSE ESTIMATING METHOD OF MRI BASED COMPOSITE IMAGE USING LOOKUP TABLE

(71) Applicant: CATHOLIC UNIVERSITY INDUSTRY-ACADEMIC COOPERATION FOUNDATION, Seoul (KR)

(72) Inventors: Young-Nam Kang, Seoul (KR); Shin-Wook Kim, Incheon (KR); Jina Kim, Gyeongsangnam-do (KR); Hun-joo Shin, Incheon (KR); Hyeong-Wook Park, Seoul (KR); Chul-Seung Kay, Gyeonggi-do (KR); Ki-jun Kim, Gyeonggi-do (KR); Jin-Sol Shin, Gyeonggi-do (KR)

(73) Assignee: Catholic University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/762,987

(22) PCT Filed: Mar. 23, 2017

(86) PCT No.: PCT/KR2017/003095
§ 371 (c)(1),
(2) Date: Mar. 23, 2018

(87) PCT Pub. No.: WO2018/021652
PCT Pub. Date: Feb. 1, 2018

(65) Prior Publication Data
US 2019/0269346 A1    Sep. 5, 2019

(30) Foreign Application Priority Data
Jul. 28, 2016 (KR) ........................ 10-2016-0096286

(51) Int. Cl.
*A61B 5/055* (2006.01)
*A61B 6/03* (2006.01)
(Continued)

(52) U.S. Cl.
CPC ................ *A61B 5/055* (2013.01); *A61B 6/00* (2013.01); *A61B 6/03* (2013.01); *G01R 33/00* (2013.01);
(Continued)

(58) Field of Classification Search
CPC .......... A61B 5/055; A61B 6/03; A61B 6/037; A61B 2503/045; A61B 5/0263; G06T 2207/10088; G01R 33/56; G01R 33/4812
(Continued)

(56) References Cited

U.S. PATENT DOCUMENTS

| 2006/0058605 A1* | 3/2006 | Deischinger | A61B 8/00 600/407 |
| 2010/0204563 A1* | 8/2010 | Stodilka | G01R 33/481 600/411 |
| 2014/0039517 A1* | 2/2014 | Bowling | B25J 13/00 606/130 |

FOREIGN PATENT DOCUMENTS

| JP | 2010-082031 A | 4/2010 |
| JP | 5270892 B2 | 8/2013 |

(Continued)

OTHER PUBLICATIONS

International Search Report issued in connection with PCT/KR2017/003095.

*Primary Examiner* — Melissa J Koval
*Assistant Examiner* — Trung Nguyen
(74) *Attorney, Agent, or Firm* — Akerman LLP

(57) ABSTRACT

The present invention relates to a radiation amount estimating method, and more particularly, to a radiation amount
(Continued)

estimating method of an MRI based composite image using a lookup table. To this end, the object of the present invention is to provide a radiation dose estimating method of an MRI based composite image using a lookup table including: generating a lookup table representing a linear attenuation coefficient of a region of interest from a CT image (S100); photographing at least two of a T1 image, a T2 image, and a PETRA image of a patient from MRI equipment (S120); generating a composite image by superimposing the photographed images (S140); representing a border line of the region of interest in the composite image to distinguish the region of interest (S160); designating the linear attenuation coefficient of the lookup table in the distinguished region of interest (S180); and estimating a radiation dose based on the composite image to which the linear attenuation coefficient is designated (S200).

1 Claim, 14 Drawing Sheets

(51) Int. Cl.
  *G01R 33/48* (2006.01)
  *G01R 33/56* (2006.01)
  *G01R 33/00* (2006.01)
  *A61B 6/00* (2006.01)
(52) U.S. Cl.
  CPC ......... *G01R 33/4812* (2013.01); *G01R 33/56* (2013.01); *G06T 2207/10088* (2013.01)
(58) Field of Classification Search
  USPC ........ 324/300, 307, 332, 344, 500, 501, 702
  See application file for complete search history.

(56) References Cited

FOREIGN PATENT DOCUMENTS

| | | |
|---|---|---|
| JP | 2014-215238 A | 11/2014 |
| JP | 5741980 B2 | 7/2015 |
| WO | 2015/175848 A1 | 11/2015 |

* cited by examiner

| Patients | Brain | Eyeball | Cavity | Bone |
| --- | --- | --- | --- | --- |
| 1 | 739 | 329 | 98 | 1277 |
| 2 | 701 | 283 | 21 | 1362 |
| 3 | 747 | 306 | 54 | 1261 |
| 4 | 778 | 328 | 15 | 1414 |
| 5 | 721 | 318 | 17 | 1119 |
| 6 | 616 | 307 | 9.9 | 1217 |
| 7 | 624 | 294 | 65 | 1223 |
| 8 | 539 | 226 | 16 | 1024 |
| 9 | 694 | 305 | 19 | 1178 |
| 10 | 719 | 307 | 39 | 1152 |
| 11 | 645 | 292 | 45 | 1220 |
| 12 | 637 | 275 | 14 | 1182 |
| 13 | 533 | 235 | 19 | 1116 |
| 14 | 658 | 293 | 9.7 | 1348 |
| 15 | 652 | 294 | 9.6 | 1207 |
| range | 533-739 | 226-329 | 9.6-98 | 1024-1414 |

FIG. 7

RADIATION DOSE ESTIMATING METHOD OF MRI BASED COMPOSITE IMAGE USING LOOKUP TABLE

This application is a national phase of PCT/KR2017/003095, filed Mar. 23, 2017, and claims priority to KR 10-2016-0096286, filed Jul. 28, 2016, the entire contents of both of which are hereby incorporated by reference.

TECHNICAL FIELD

The present invention relates to a radiation dose estimating method, and more particularly, to a radiation dose estimating method of an MRI based composite image using a lookup table.

BACKGROUND ART

Recently, as radiology develops, computed tomography (CT) or magnetic resonance imaging (MRI) is frequently used for surgery or pre-treatment checkup. Since an internal status of a patient can be checked by reading a photograph and a 3D modeling thereof is also possible, such a medical technology is recognized as a very efficient test method.

CT imaging (or CT scan) has an advantage in that an accurate cross-sectional image is obtained and has a disadvantage in that a large amount of radiation needs to be irradiated so that a patient is inevitably exposed to the radiation. Nevertheless, CT imaging is used because it is highly accurate and it is easy to calculate a radiation dose (hereinafter, referred to as a "dose") through a black and white photograph. In contrast, since a contrast of a tissue in the CT image is low, it is difficult to distinguish between a normal tissue and a tumor.

In the meantime, the MRI imaging uses a high frequency wave instead of radiation, so that it is stable because there is no risk of exposure to the radiation. Further, the MRI imaging may be performed to freely select a necessary angle in the body and have an excellent resolution. Therefore, in order to reduce an exposure amount to the patient, the radiology is gradually shifted from the CT imaging to the MRI imaging. However, the MIR image has an advantage in that a tumor is easily distinguished but has a disadvantage in that the MIR imaging does not use radiation so that it is difficult to calculate a dose.

Various methods have been proposed to take the advantage and overcome the disadvantage in consideration of the advantages and disadvantages of the CT imaging and MIR imaging.

One of these methodologies is to generate a composite CT image. For example, FIG. 1 is a CT image of the related art obtained by imaging a plurality of patients, FIG. 2 is a composite CT image generated by superimposing the plurality of CT images illustrated in FIG. 1, FIG. 3 is an MRI image of the related art, FIG. 4 is an image obtained by superimposing an MR simulation image of the related art and a composite CT image and then manually representing a boundary of a region of interest, and FIG. 5 is an image representing a state in which a linear attenuation coefficient is designated to the region of interest bordered in FIG. 4.

As illustrated in FIGS. 1 to 5, the composite CT image as illustrated in FIG. 2 is generated from the plurality of CT images as illustrated in FIG. 1 and is superimposed with the MR simulation image as illustrated in FIG. 3. Thereafter, a boundary of a region of interest is manually represented (see FIG. 4). Next, a linear attenuation coefficient (LAC) is designated to the region of interest bordered as illustrated in FIG. 5. A distribution diagram of a radiation dose may be obtained using one to one matching of contrast enhancement (Hounsfield unit: HU) based on the image as illustrated in FIG. 5.

However, the related art method has the following disadvantages. That is, the composite CT image uses an average value but eventually, the CT imaging needs to be performed one time. Further, when the plurality of images is superimposed, a geographical position error is incurred. Furthermore, since the average value is used, it is not CT data of an actual patient. Further, the boundary of the region of interest is manually drawn while visibly checking the boundary so that it is inconvenience and inaccurate.

DISCLOSURE

Technical Problem

Therefore, the present invention has been made to solve the above-described problems and an object of the present invention is to provide a radiation dose estimating method of an MRI based composite image using a lookup table which may accurately estimate a cumulative radiation dose only by MRI imaging without performing CT imaging for radiotherapy and diagnostic imaging.

Technical Solution

An object of the present invention may be achieved by a radiation dose estimating method of an MRI based composite image using a lookup table including: generating a lookup table representing a linear attenuation coefficient of a region of interest from a CT image (S100); photographing at least two of a T1 image, a T2 image, and a PETRA image of a patient from MRI equipment (S120); generating a composite image by superimposing the photographed images (S140); representing a border line of the region of interest in the composite image to distinguish the region of interest (S160); designating the linear attenuation coefficient of the lookup table to the distinguished region of interest (S180); and estimating a radiation dose based on the composite image to which the linear attenuation coefficient is designated (S200).

The generating of a lookup table (S100) may be performed based on CT images of a plurality of patients.

The region of interest may include at least one of a brain, an eyeball, a cavity, and a bone.

In the generating of a composite image (S140), the T1 image and the PETRA image may be superimposed, the T2 image and the PETRA image may be superimposed, or the T1 image, the T2 image, and the PETRA image may be superimposed to generate a composite image.

In the representing of a border line of the region of interest (S160), the border line may be represented based on a gray scale or a CT number of each pixel of the composite image.

In the designating of a linear attenuation coefficient (S180), the linear attenuation coefficient may be designated using an average value in the linear attenuation coefficient range of the region of interest in the lookup table.

Further, in the estimating of a radiation dose (S200), the radiation dose may be estimated using one to one matching of the contrast enhancement (Hounsfield unit: HU).

Advantageous Effects

According to an exemplary embodiment of the present invention, it is possible to accurately estimate a cumulative radiation dose only by MRI imaging without performing CT imaging for radiotherapy and diagnostic image capturing. Therefore, the patient may be out of a risk of radiation exposure.

Further, there is an advantage in that a composite image may be generated from the MRI image, as if it is generated by the CT imaging. Moreover, an image from which a normal tissue and a tumor can be distinctly distinguished is obtained so that it is usefully used for a radiation therapy.

DESCRIPTION OF DRAWINGS

The accompanying drawings in the specification illustrate an exemplary embodiment of the present disclosure. The technical spirit of the present disclosure will be more clearly understood from the following detailed description taken in conjunction with the accompanying drawings. Therefore, the present invention will not be interpreted to be limited to the drawings.

(a) of FIG. 6 is a flowchart illustrating a radiation dose estimating method of an MRI based composite image using a lookup table according to an exemplary embodiment of the present invention.

(b) of FIG. 6 is a flowchart of a specific step of forming a border line of a region of interest of an exemplary embodiment of the present invention.

FIG. 7 is an example of a lookup table formed of linear attenuation coefficients extracted from CT images of a plurality of patients, to be used in the present invention.

Figure 8:

FIG. 8 is an example of a T1 image.

Figure 9:

FIG. 9 is an example of a T2 image.

Figure 10:

FIG. 10 is an example of a PETRA image.

Figure 11:

FIG. 11 is an example of a composite image generated according to the present invention when a region of interest is an eyeball.

Figure 12:
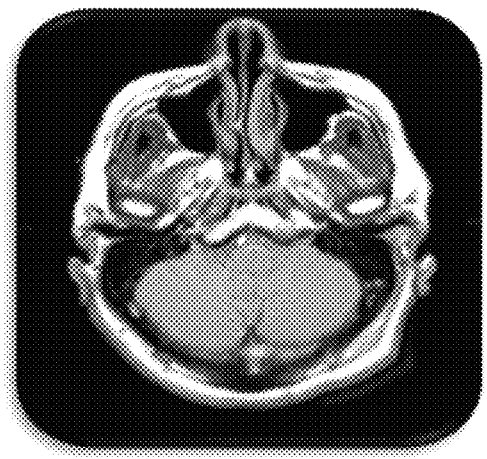

FIG. 12 is an example of a composite image generated according to the present invention when a region of interest is a cavity.

Figure 13:

FIG. 13 is an example of a composite image generated according to the present invention when a region of interest is a bone.

Figure 14:
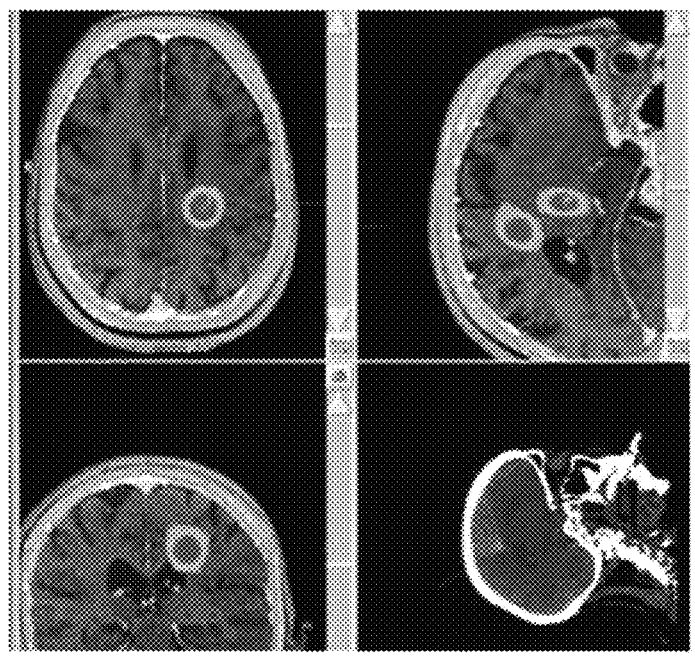
Figure 15A:
Figure 15B:
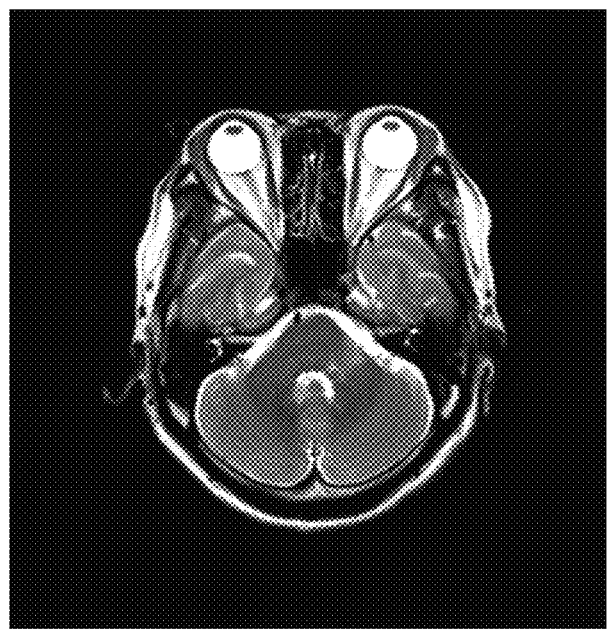
Figure 15C:
Figure 15D:
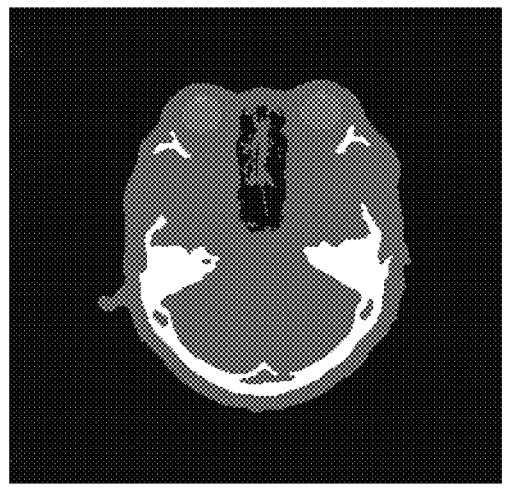

FIG. 14 is an example of a result image obtained by estimating a radiation dose using one to one matching of contrast enhancement (Hounsfield unit: HU) based on the composite image of FIGS. 11 to 13.

FIG. 15 is a specific image of an exemplary embodiment of the present invention in which (a) of FIG. 15 is a T1-weighted MR image, (b) of FIG. 15 is a T2-weighted MR image, (c) of FIG. 15 is a PETRA MR image, and (d) of FIG. 15 is a composite CT image generated according to (b) of FIG. 6.

BEST MODE

Hereinafter, a configuration of the present invention will be described in more detail with reference to the accompanying drawings. Those skilled in the art may make various modifications to the present invention and the present invention may have various embodiments thereof, and thus specific embodiments will be illustrated in the drawings and described in detail in the detailed description.

In the present invention, it should be understood that terminology "include" or "have" indicates that a feature, a number, a step, an operation, a component, a part or the combination thoseof described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms which are defined in a generally used dictionary should be interpreted to have the same meaning as the meaning in the context of the related art but are not interpreted as an ideally or excessively formal meaning if it is not clearly defined in the present invention.

Hereinafter, a radiation dose estimating method of an MRI based composite image using a lookup table according to an exemplary embodiment of the present invention will be described in detail with reference to the accompanying drawings. (a) of FIG. 6 is a flowchart illustrating a radiation dose estimating method of an MRI based composite image using a lookup table according to an exemplary embodiment of the present invention. As illustrated in (a) of FIG. 6, first, a lookup table representing a linear attenuation coefficient of a region of interest is generated from a CT image (S100).

FIG. 7 is an example of a lookup table formed of linear attenuation coefficients extracted from CT images of a plurality of patients to be used in the present invention. As illustrated in FIG. 7, CT images for 15 patients are photographed and then grayscale values for regions of interest (for example, a brain, an eyeball, a cavity, and a bone) are read out. A range of the grayscales is 0 to 65535 and a grayscale of "0" indicates black and a grayscale of "65535" indicates white. The grayscale values may be simply converted into a linear attenuation coefficient. It is understood from the lookup table of FIG. 7 that a grayscale value of each region of interest forms a predetermined range. For example, it is understood that a range of a grayscale of the brain (a) is 533 to 739, a range of a grayscale of the eyeball (b) is 226 to 329, a range of a grayscale of the cavity (c) is 9.6 to 98, and a range of a grayscale of the bone (d) is 1024 to 1414. As the CT image for creating the lookup table, it is desirable to utilize recorded matters which have been photographed and stored in existing hospitals rather than a newly photographed CT image. When the number of cases (the number of patients) is larger, it is more desirable.

Next, a T1 image, a T2 image, and a pointwise echo time reduction with radial acquisition (PETRA) image of the patient are photographed using MRI equipment (S120). The T1, T2, and PETRA images are different MRI images obtained by photographing the same part of the same patient at the same time zone. FIG. 8 is an example of the TI image photographed by the above-mentioned method, FIG. 9 is an example of the T2 image, and FIG. 10 is an example of the PETRA image.

For reference, the higher the fat content, the higher the signal intensity of the T1 image (looks white). From a brain image, signal intensities are sorted in this order of a fat tissue>a white matter>a gray matter>CSF. Most lesions contain lots of water (edema due to inflammation or tumors having rich blood flow) and look like a low signal intensity (black) in the T1 image.

The higher the water, the higher the signal intensity of the T2 image (looks white). From the brain image, signal intensities are sorted in the order of CSF>the gray matter>the white matter>the fat tissue and the lesions look like a high signal intensity (white) in the T2 image. That is, in order to quickly find the lesions, a portion which appears to have a high signal intensity (white) needs to be found from the T2 image first. A difference between the T1 image and the T2 image is represented in the following tables.

TABLE 1

| Classification | T1 | T2 |
|---|---|---|
| Water | Black | White |
| Fat | White | Black |

TABLE 2

| Classification | T1 | T2 |
|---|---|---|
| Ventricle | Black | White |
| White matter | White | Black |
| Gray matter | Gray | Gray |
| Calcification, bone | Black | Black |

White parts of the T1 image and the T2 image are colors of the ventricles. The ventricle is fully full of water. Therefore, a portion where water is represented in black is a T1 enhanced image and a portion where water is represented in white is a T2 enhanced image. That is, the T2 image is similar to a negative image of the CT and the T1 image and, the T2 image may be distinguished from the color of the ventricle.

Next, in the gray matter, somas exist. In the gray matter, water and fats are mixed half and half. A cell wall which forms the soma is formed of fat but contents of the soma are mainly water. Therefore, the gray matter which is a mass of somas is water and fats. Therefore, both the T1 image and the T2 image are gray in which black and white are mixed.

Finally, in the bone and calcification, signals are searched from both images in the MRI image. The signals are mainly caused by water. Therefore, signals in the bone or calcification where the content of water is small are small, so that both the T1 and T2 images are black.

The PETRA image represents to distinguish between air and tissues so that an outline of a body is well represented and a bone is well distinguished in the body. Therefore, when the PETRA image is superimposed with the T1 image and the T2 image, it helps to reduce a geometrical error.

Next, the photographed T1, T2, and PETRA images are superimposed to generate a composite image (S140). FIG. 11 is an example of a composite image generated according to the present invention when a region of interest is an eyeball, FIG. 12 is an example of a composite image generated according to the present invention when a region of interest is a cavity, and FIG. 13 is an example of a composite image generated according to the present invention when a region of interest is a bone.

As illustrated in FIGS. 11 to 13, three images may be superimposed while minimizing a geometrical error and an image in which boundaries between the region of interest and air and between the region of interest and a peripheral tissue are clear may be obtained. The clear image as described above may help to define the boundary in the next step.

Next, a border line of the region of interest is represented in the composite image to distinguish the region of interest (S160). The border line may be collectively distinguished by a known method (for example, an image outline enhancer) using a software based on a grayscale value and a contrast of each pixel.

Next, a linear attenuation coefficient of the lookup table is designated to the region of interest which is automatically distinguished by the software (S180). For example, in the lookup table as illustrated in FIG. 7, a range of a grayscale of the brain is 533 to 739, a range of a grayscale of the eyeball is 226 to 329, a range of a grayscale of the cavity is 9.6 to 98, and a range of a grayscale of the bone is 1024 to 1414. When the linear attenuation coefficient is designated, an average value or a median value of the ranged values is designated.

Next, a radiation dose is estimated based on the composite image in which the linear attenuation coefficient is designated to each region of interest (S200). The radiation dose is estimated using one to one matching of contrast enhancement (Hounsfield unit: HU). When the HU method is used, a distribution map of the radiation dose may be obtained. FIG. 14 is an example of a result image obtained by estimating a radiation dose using one to one matching of contrast enhancement (Hounsfield unit: HU) based on the composite image of FIGS. 11 to 13. As illustrated in FIG. 14, it is understood that an area where the radiation dose is concentrated is represented in red and an area where a lower radiation dose is concentrated is represented in green. Therefore, a doctor may confirm an area where the radiation dose is concentrated through the image as illustrated in FIG. 14 and the area may be utilized for a treatment later. For reference, the HU has a value in the range of −1000 to +1000.

(b) of FIG. 6 is a flowchart of a specific step of forming a boundary of a region of interest of an exemplary embodiment of the present invention, and FIG. 15 is a specific image of an exemplary embodiment of the present invention in which (a) of FIG. 15 is a T1-weighted MR image, (b) of FIG. 15 is a T2-weighted MR image, (c) of FIG. 15 is a PETRA MR image, and (d) of FIG. 15 is a composite CT image generated according to (b) of FIG. 6. That is, (a) to (c) of FIG. 15 are to obtain MR images and (d) of FIG. 15 is to calculate a dose. As illustrated in (b) of FIG. 6 and FIG. 15, one of regions of interest (for example, a body, air, an eyeball, a lens, a cavity, a ventricle, a brain stem, and a bone) is designated (S300).

Next, a border line is distinguished in the designated region of interest (for example, the body) using a software algorithm (S310).

Next, contrast enhancement is performed in the generated border line (a closed curve) (S330). The above-described process is sequentially repeated for the air, the eyeball, the lens, the cavity, the ventricle, the brain stem, and the bond (S390).

Finally, a CT image (see (d) of FIG. 15) composed by combining the results of the contrast enhancement which has been performed so far is generated (S370).

MODE FOR THE INVENTION

Although the present invention is described with reference to the above-mentioned exemplary embodiment, those skilled in the art may recognize that various modifications and changes can be made without departing from the gist and the scope of the present invention. Further, it is obvious that the changes and modifications are included within the scope of the accompanying claims.

INDUSTRIAL APPLICABILITY

The present invention relates to a radiation amount estimating method, and more particularly, to a radiation amount estimating method of an MRI based composite image using a lookup table.

DRAWINGS

Figure 1:
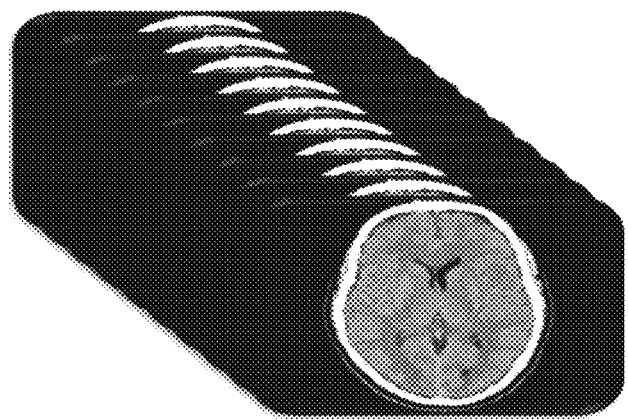
FIG. 1 is a CT image of the related art obtained by imaging a plurality of patients.
Figure 2:
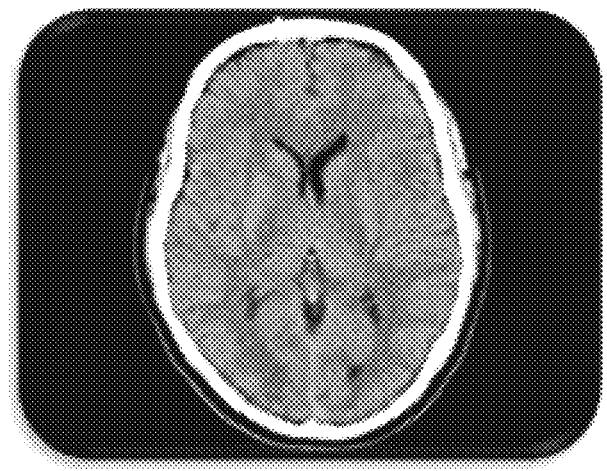
FIG. 2 is a composite CT image generated by superimposing a plurality of images illustrated in FIG. 1.
Figure 3:
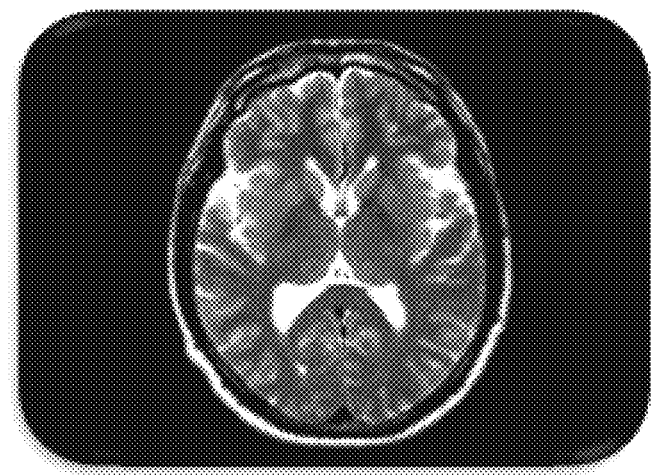
FIG. 3 is an MRI image of the related art.
Figure 4:
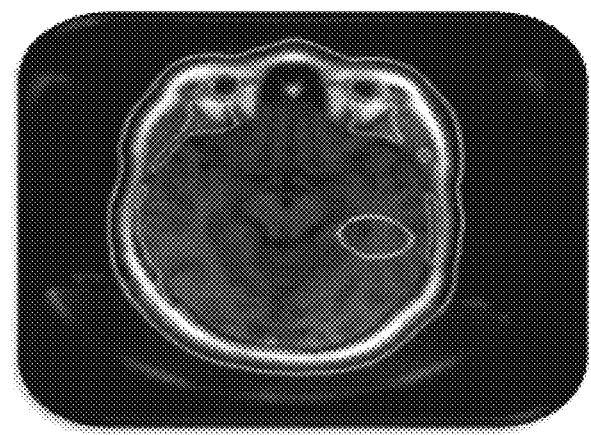
FIG. 4 is an image obtained by superimposing an MR simulation image of the related art and a composite CT image and then manually representing a boundary of a region of interest.
Figure 5:
FIG. 5 is an image representing a state in which a linear attenuation coefficient is designated to a region of interest bordered in FIG. 4.
Figure 6A:
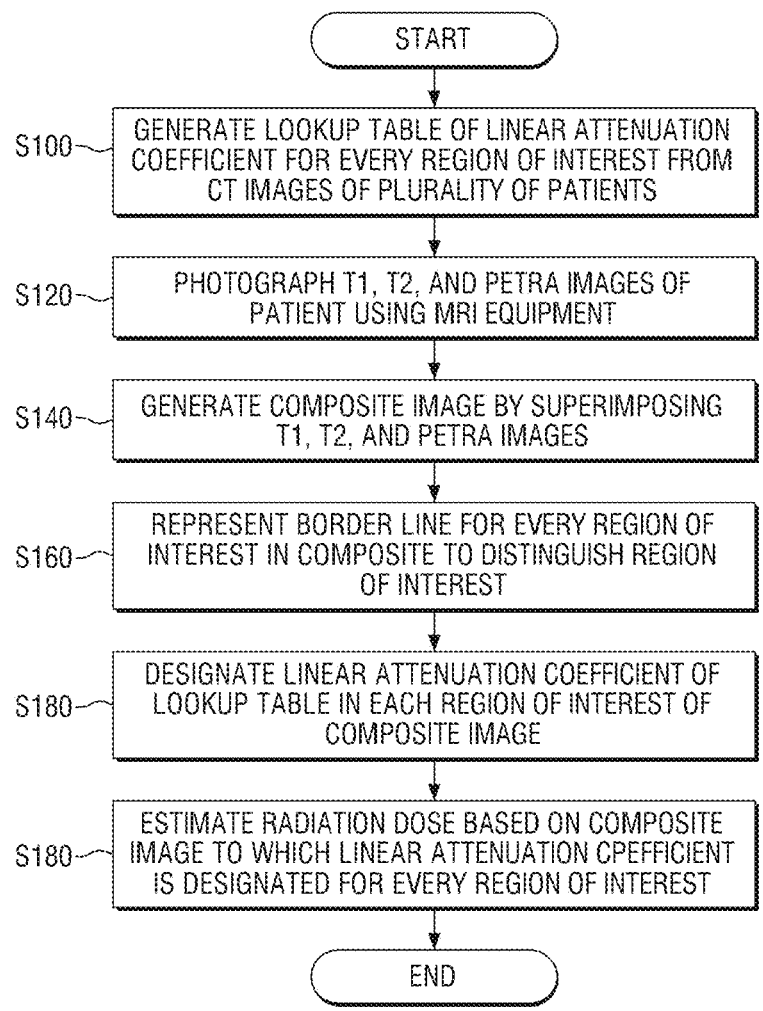
Figure 6B:
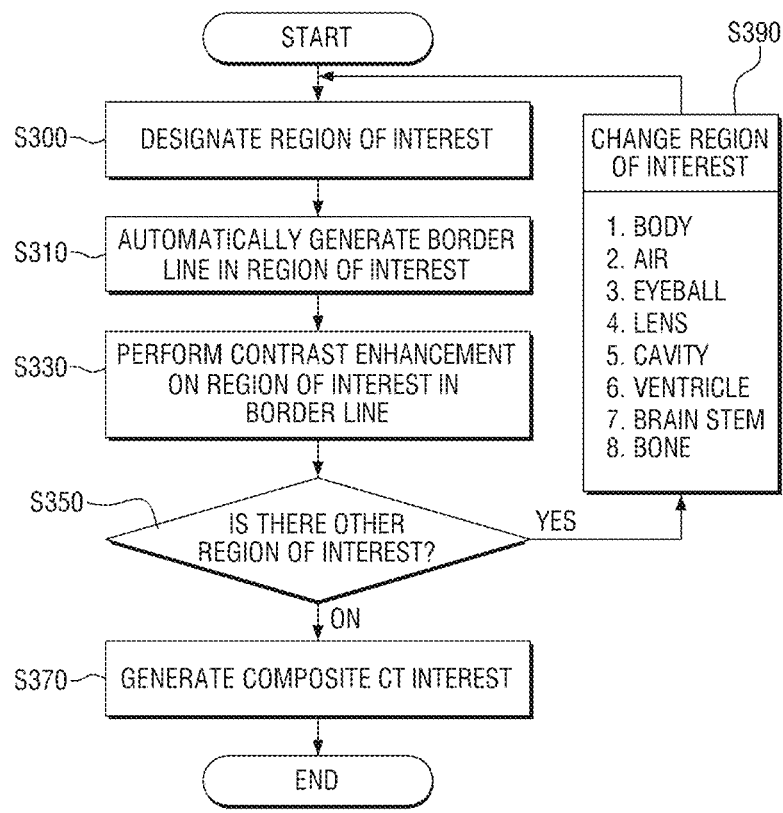

[FIG. 6A]
START
S100: GENERATE LOOKUP TABLE OF LINEAR ATTENUATION COEFFICIENT FOR EVERY REGION OF INTEREST FROM CT IMAGES OF PLURALITY OF PATIENTS
S120: PHOTOGRAPH T1, T2, AND PETRA IMAGES OF PATIENT USING MRI EQUIPMENT
S140: GENERATE COMPOSITE IMAGE BY SUPERIMPOSING T1, T2, AND PETRA IMAGES
S160: REPRESENT BORDER LINE FOR EVERY REGION OF INTEREST IN COMPOSITE IMAGE TO DISTINGUISH REGION OF INTEREST
S180: DESIGNATE LINEAR ATTENUATION COEFFICIENT OF LOOKUP TABLE IN EACH REGION OF INTEREST OF COMPOSITE IMAGE
S200: ESTIMATE RADIATION DOSE BASED ON COMPOSITE IMAGE TO WHICH LINEAR ATTENUATION COEFFICIENT IS DESIGNATED FOR EVERY REGION OF INTEREST
END
[FIG. 6B]
START
S300: DESIGNATE REGION OF INTEREST
S310: AUTOMATICALLY GENERATE BORDER LINE IN REGION OF INTEREST
S330: PERFORM CONTRAST ENHANCEMENT ON REGION OF INTEREST IN BORDER LINE
S350: IS THERE OTHER REGION OF INTEREST?
예 : YES
아니오 : NO
S370: GENERATE COMPOSITE CT IMAGE
END
S390: CHANGE REGION OF INTEREST

1: BODY
2: AIR
3: EYEBALL
4: LENS
5: CAVITY
6: VENTRICLE
7: BRAIN STEM
8. BONE

The invention claimed is:

1. A radiation dose estimating method of an MRI based composite image using a lookup table, the method comprising:
generating a lookup table representing a linear attenuation coefficient of a region of interest from a CT image;
photographing at least two of a T1 image, a T2 image, and a PETRA image of a patient from MRI equipment;
generating a composite image by superimposing the photographed images;
representing a border line of the region of interest in the composite image to distinguish the region of interest;
designating the linear attenuation coefficient of the lookup table to the distinguished region of interest; and
estimating a radiation dose based on the composite image to which the linear attenuation coefficient is designated;
wherein the generating of a lookup table is performed based on CT images of a plurality of patients;
wherein the region of interest includes at least one of a brain, an eyeball, a cavity, and a bone;
wherein in the generating of a composite image, the T1 image and the PETRA image are superimposed, the T2 image and the PETRA image are superimposed, or the T1 image, the T2 image, and the PETRA image are superimposed to generate a composite image;
wherein in the representing of a border line of the region of interest, the border line is represented based on a gray scale or a CT number of each pixel of the composite image;
wherein in the designating of a linear attenuation coefficient, the linear attenuation coefficient is designated using an average value in the linear attenuation coefficient range of the region of interest in the lookup table; and
wherein in the estimating of a radiation dose, the radiation dose is estimated using one to one matching of a contrast enhancement (Hounsfield unit: HU).

* * * * *